United States Patent [19]

McFadden et al.

[11] 4,101,559

[45] Jul. 18, 1978

[54] PRECURSORS OF HETEROFURANOBENZOXEPIN ACETIC ACIDS

[75] Inventors: Arthur Raymond McFadden, East Brunswick; Daniel Eugene Aultz, Middlesex, both of N.J.

[73] Assignee: American Hoechst Corporation, Bridgewater, N.J.

[21] Appl. No.: 788,788

[22] Filed: Apr. 19, 1977

Related U.S. Application Data

[62] Division of Ser. No. 607,926, Aug. 26, 1975, Pat. No. 4,025,640.

[51] Int. Cl.² .......................................... C07D 307/68

[52] U.S. Cl. ............................... 260/347.3; 260/347.5

[58] Field of Search ........................... 260/347.3, 347.5

[56] References Cited

PUBLICATIONS

Andrisano, Chemical Abstracts, vol. 45 (1951) 602e.

*Primary Examiner*—Richard L. Raymond
*Attorney, Agent, or Firm*—Curtis, Morris & Safford

[57] ABSTRACT

Heteroarylbenzoxepin-acetic acids, esters thereof, novel precursors thereof, pharmaceutically acceptable salts thereof and processes for their preparation are disclosed. These compounds are useful as antiinflammatory and analgesic agents.

4 Claims, No Drawings

PRECURSORS OF HETEROFURANOBENZOXEPIN ACETIC ACIDS

This is a division of application Ser. No. 607,926, filed Aug. 26, 1975, now U.S. Pat. No. 4,025,926.

This invention relates to heteroarylbenzoxepin-acetic acids, esters and precursors thereof and pharmaceutically acceptable salts thereof having antiinflammatory and analgesic activity.

To the best of our knowledge, the compounds of the present invention have not heretofore been described. Sulfur compounds of the formula:

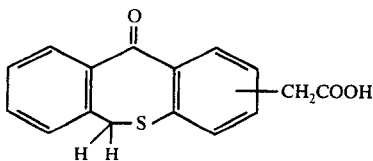

and derivatives thereof are mentioned as having analgesic, antipyretic and antiinflammatory activity in Japanese Patent Publication No. 72 00 425, published Jan. 7, 1972. United States Patent Application of Helsley et al., Ser. No. 459,774, filed Apr. 10, 1974, teaches 6,11-dihydrodibenz[b,e]oxepin-acetic acids and derivatives thereof demonstrating antiinflammtory and analgesic activity. The tricyclic compounds of the present invention have significant structural differences and display unanticipated good activity.

The compounds of the invention have the formulae

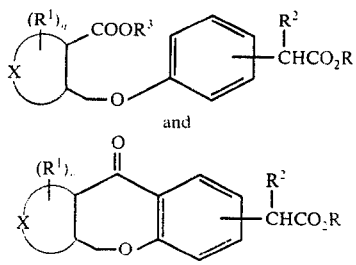

wherein X, together with the carbon atoms to which it is attached, is a furano ring structure; R is hydrogen or straight or branched chain alkyl of from 1 to 5 carbon atoms; $R^1$ is lower alkyl of 1 to 4 carbon atoms; $R^2$ is hydrogen or methyl; $R^3$ is hydrogen or lower alkyl of 1 to 4 carbon atoms; and $n$ is the integer 0, 1 or 2; and pharmaceutically acceptable salts thereof prepared from suitable bases. Contemplated as separate embodiments of the invention are the dicarboxylic acids and tricyclic compounds. Also contemplated to be separate embodiments are the carboxylic acids (R is hydrogen) and esters thereof (R is alkyl). Preferred compounds are those wherein the furano ring is unsubstituted.

The compounds of the present invention are prepared by one of the methods below.

METHOD A

1. A lower alkyl ester, an ester with 1 to 4 carbon atoms in the alcoholic unit, of the formula

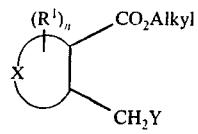

wherein X together with the carbon atoms to which it attaches, $R^1$ and n are as defined earlier and Y is halogen, is allowed to react with a lower alkyl ester of a (hydroxyphenyl)acetic acid in the presence of a solvent such as acetone, butanone, ethanol or dimethylformamide, an acid scavenger such as potassium carbonate or sodium ethoxide and with or without a reaction initiator such as potassium or sodium iodide at a temperature of from ambient to the boiling point of the solvent for from a few minutes to 72 hours to provide a corresponding diester of the formula

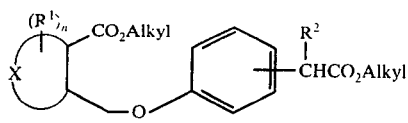

2. Saponifying the diester to its corresponding dicarboxylic acid by a suitable method known to the art. A preferred method utilizes a base such as sodium or potassium hydroxide in a solvent such as aqueous ethanol or water for a time of from 15 minutes to 24 hours and at a temperature of from ambient to the boiling point of the solvent.

3. The dicarboxylic acid is cyclized by treatment with a dehydrating agent such as polyphosphoric acid, ethanol-phosphorus pentoxide or sulfuric acid, with or without a solvent such as tetramethylenesulfone or acetic acid, at a temperature of from 50° to 125° C. and for a time of from 5 minutes to 12 hours to provide a heteroarylbenzoxepin-acetic acid, a compound of the invention of the formula

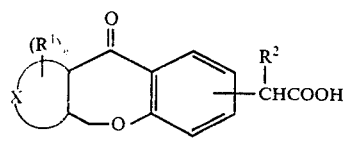

METHOD B

1. A diacid halide is prepared by the treatment of a dicarboxylic acid, prepared above in Method A, step 2, with a sufficient amount of an agent such as thionyl halide or phosphorus pentahalide in the presence or absence of a solvent, at a temperature of from ambient to the reflux point of the reaction mixture, and for from 15 minutes to 6 hours.

2. The diacid halide is cyclized under Friedel-Carfts conditions and then hydrolyzed by a method known to the art to provide a compound of the invention as defined in Method A, step 3. A preferred method of cyclization utilizes a Lewis acid such as stannic chloride at ambient temperature. Alternatively the diacid halide can be subjected to thermal cyclization by heating to a temperature of from 80° to 125° C. for from 10 minutes to 24 hours and then hydrolyzed to produce a compound of the invention.

METHOD C

A compound of the invention, prepared by either Method A or B, is esterified by allowing it to react with an alcohol of the formula ROH; wherein R is as defined earlier, in the presence of an acid such as sulfuric, hydrochloric or p-toluenesulfonic, at a temperature of from 50° C. to the boiling point of the alcohol, and for from 15 minutes to 24 hours.

As well known to those skilled in the art, reaction times are correlated to the reaction temperatures in the sense that shorter times are needed when using higher temperature.

The tricyclic compounds of the present invention are useful as systemic antiinflammatory agents due to their ability to suppress inflammation in mammals. The activity of the compounds is demonstrated in the carrageenin induced rat paw edema antiinflammatory assay [Proc. Soc. Exptl. Biol. Med., III, 544 (1962); J. Pharmacol. Exp. Ther., 141, 369 (1963)]. For example, at oral doses of 3.6, 4.2 and 24 mg/kg of body weight respectively, 4,10-dihydro-10-oxothieno[3,2-c][1]benzoxepin-8-acetic acid, methyl 4,10-dihydro-10-oxothieno[3,2-c][1]-benzoxepin-8-acetate and 4,10-dihydro-10-oxofurano[3,2-c]-[1]benzoxepin-8-acetic acid, exhibit an approximately 50% of edema.

The tricyclic compounds of the present invention are also useful as topical antiinflammatory agents due to their ability to suppress dermal inflammation in mammals. The activity of representative compounds is demonstrated in the croton oil induced edema assay in mice [Endocrinology, 77, 625 (1965); Clin, Pharmacol. and Therap., 16, 900 (1974)]. For example, when applied topically at concentrations of 2.5% and 5% respectively, 4,10-dihydro-10-oxothieno[3,2-c][1]benzoxepin-8-acetic acid and methyl 4,10-dihydro-10-oxothieno[3,2-c][1]benzoxepin-8-acetate exhibit, respectively, a 65 and 24% inhibition of edema.

The tricyclic compounds of the present invention are also useful as analgesic agents due to their ability to alleviate pain in mammals. Representative compounds of the invention demonstrate this activity in the 2-phenyl-1,4-benzoquinone-induced writhing test in mice, a standard assay for analgesia [Proc. Soc. Expt]. Biol. Med., 95, 729 (1957)]. For example, at oral doses of 4.5 and 45.0 mg/kg of body weight, 4,10-dihydro-10-oxothieno-[3,2-c][1]benzoxepin-8-acetic acid and 4,10-dihydro-10-oxofurano-[3,2-c][1]benzoxepin-8-acetic acid, respectively, exhibit an approximately 50% inhibition of edema.

These data illustrate that the compounds of this invention are useful as systemic antiinflammatory and/or analgesic agents at a dose of from 0.1 to 50 mg/kg of body weight and as topical antiinflammatory agents at concentrations of from 0.1 to 20%.

Examples of compounds of the invention include:

4,10-dihydro-10-oxothieno[3,4-c][1]benzoxepin-7-acetic acid;
Ethyl 4,10-dihydro-10-oxofurano[3,2-c][1]benzoxepin-8-acetate;
Amyl 4,10-dihydro-1,2,3-trimethyl-10-oxopyrrolo-[3,4-c][1]benzoxepin-8-acetic acid;
5,11-dihydro-11-oxopyrazino[2,3-c][1]benzoxepin-8-acetic acid;
5,11-dihydro-11-oxopyrimido[4,5-c][1]benzoxepin-9-acetic acid;
n-Propyl 4,10-dihydro-10-oxooxazolo[4,5-c][1]benzoxepin-8-acetate;
4,10-dihydro-10-oxothiazolo[4,5-c][1]benzoxepin-8-acetic acid;
n-Butyl 4,10-dihydro-10-oxoimidazo[4,5-c][1]benzoxepin-7-acetate;
4,10-dihydro-10-oxothieno[2,3-c][1]benzoxepin-8-acetic acid;
4,10-dihydro-α-methyl-10-oxothieno[3,2-c][1]benzoxepin-8-acetic acid;
4,10-dihydro-α-methyl-10-oxofurano[2,3-c][1]benzoxepin-7-acetic acid; and
4,10-dihydro-10-oxoisoxazolo[4,5-c][1]benzoxepin-8-acetic acid.

Effective quantities of the tricyclic compounds of the invention may be administered to a patient by any one of various methods, for example, orally as in capsules or tablets, topically as in ointments, solutions or salves, parenterally in the form of sterile solutions or suspensions, and in some cases intraveneously in the form of sterile solutions. The free acid final products, while effective themselves, may be formulated and administered in the form of their pharmaceutically acceptable addition salts for purposes of stability, convenience of crystallization, increased solubility and the like. Such salts include those of sodium, potassium, calcium, magnesium or ammonium.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–500 milligrams of active compound.

The tablets, pills, capsules, troches, and the like may also contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as fatty oil. Other dosage unit forms may contain other various materials which modify the physical form of the dosage unit for example, as coatings. Thus, tablets or pills may be coated with sugar, Shellac, or other enteric coating agents. A syrup may contain, in addition to the active compounds, sucrose as a sweetening agent, and certain preservatives, dyes and colorings, and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied to be between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenter preparation can be enclosed in ampules, disposable syringes or multiple dose vials made of glass or plastic.

For the purpose of topical administration, the active compounds of the invention may be incorporated into a solution, suspension, ointment, cream or salve. These preparations should contain at least 0.01% of active compound but may be varied to be between 0.05 and about 20% of the weight thereof. The amount of active compound in such compositions is such that suitable dosage will be obtained. Preferred topically administered preparations should contain between 0.1 and 10% of active compound.

The topical compositions may also include the following components: water, fixed oils, polyethylene glycols, glycerol, petroleum, stearic acid, beeswax, other synthetic solvents or mixtures thereof; antibacterial agents such as benzyl alcohol or methyl paraben; antioxidants such as α-tocopherol acetate; chelating agents such as ethylenediaminetetracetic acid; buffer such as acetates, citrates or phosphates; emulsifying agents such as polyoxyethylene monooleate and coloring materials and adjuvants such as ferric oxide or talc. The topical preparation can be enclosed in tubes, bottles, or jars made of metal, glass or plastic.

The invention is further illustrated by the following examples, given for illustrative purposes.

EXAMPLE 1 a. A mixture of 25.0 g of 3-bromomethyl-2-carbethoxythiophene, 18.2 g of ethyl 4-hydroxyphenylacetate, 55.2 g of potassium carbonate and 1.0 g of sodium iodide in 500 ml of butanone is refluxed for 16 hours. The salts are removed by filtration and washed with ether and the filtrate concentrated in vacuo leaving an amber oil. The oil is dissolved in ether and the ether solution washed with 5% sodium hydroxide and water, dried, filtered and the ether removed leaving a yellow oil. To a solution of the oil in 400 ml of ethanol is added 50 ml of water and 80.0 g of potassium hydroxide and the reaction mixture refluxed for 16 hours and then concentrated in vacuo. The aqueous solution is cooled and acidified with ice cold concentrated hydrochloric acid to provide a solid which is collected, dried and recrystallized from isopropanol and washed to provide beige crystals, mp 222° C., of 4-(2-carboxy-3-theinylmethoxy)phenylacetic acid.

b. To 3.5 ml of absolute ethanol is carefully added 5.80 g of phosphorus pentoxide while maintaining the temperature below 80° C. After total addition the white viscous mixture is heated at 110° C. for 1 hour and 25 ml of tetramethylenesulfone is added. The reaction temperature is adjusted to 81° to 83° C. and 2.70 g of 4-(2-carboxy-3-thienylmethoxy)phenylacetic acid introduced. The temperature of the reaction mixture is maintained for 3 hours and the mixture is carefully poured into water, basified and extracted with toluene. The aqueous phase is acidified with ice cold concentrated hydrochloric acid to provide a brown solid which is extracted with chloroform, filtered and concentrated in vacuo to a yellow solid. The solid upon trituration with ether provides light yellow cyrstals, mp 162°–164° C., of 4,10-dihydro-10-oxothieno[3,2-c][1]benzoxepin-8-acetic acid.

Analysis: Calculated for $C_{14}H_{10}SO_4$: 61.30%C; 3.68%H; 11.69%S. Found: 61.47%C; 3.73%H; 11.58%S.

EXAMPLE 2

A mixture of 0.70 g of 4,10-dihydro-10-oxothieno[3,2-c][1]benzoxepin-8-acetic acid (Example 1), 8 ml of concentrated sulfuric acid, and 150 ml of methanol is refluxed for 16 hours. The reaction mixture is concentrated in vacuo, diluted with water and extracted with benzene. The combined benzene extracts are washed with 5% sodium hydroxide and water, dried, filtered and concentrated in vacuo to an oil which solidifies upon standing. The solid is recyrstallized from methanol to provide light yellow crystals, mp 80°–81° C. of methyl 4,10-dihydro-10-oxothieno[3,2-c][1]benzoxepin-8-acetate.

Analysis: Calculated for $C_{15}H_{12}SO_4$: 62.48%C; 4.19%H; 11.12%S. Found: 62.49%C; 4.28%H; 11.27%S.

EXAMPLE 3

A solution of 1.0 g of 4,10-dihydro-10-oxothieno[3,2-c][1]benzoxepin-8-acetic acid (Example 1), 50 ml of isopropanol and 8 ml of concentrated sulfuric acid is refluxed for 16 hours and then concentrated in vacuo leaving a dark brown oil. The oil is dissolved in chloroform, washed successively with water, saturated sodium bicarbonate solution and water, dried, filtered and concentrated in vacuo leaving an amber oil which solidifies upon standing. The solid is recrystallized from isopropanol to give colorless crystals, mp 92°–94° C., of isopropyl 4,10-dihydro-10-oxothieno[3,2-c][1]benzoxepin-8-acetate.

Analysis: Calculated for $C_{17}H_{16}SO_4$: 64.54%C; 5.10%H. Found: 64.42%C; 5.17%H.

EXAMPLE 4 a. A mixture of 20.0 g of methyl 3-bromomethyl-2-furoate, 15.1 g of methyl 4-hydroxyphenyl acetate, 52.0 g of potassium carbonate and 1.0 g of sodium iodide in 360 ml butanone is treated according to the manipulative procedure described above in Example 1(a) to produce a yellow-brown precipitate which is recrystallized from acetonitrile to give off-white crystals, mp 204°–205° C., of 4-(2-carboxy-3-furylmethoxy)phenylacetic acid.

b. To a mixture of 9.6 g of 4-(2-carboxy-b 3-furylmethoxy)phenyl acetic acid in 140 ml of anhydrous benzene is added 14.4 g of phosphorus pentachloride and the suspension stirred at ambient temperature for 4 hours. The benzene is removed under reduced pressure at 85° C. to provide the diacid halide as a light tan solid. This solid is dissolved in anhydrous methylene chloride and 17.9 g of stannic chloride added portionwise over a 5 minute period. The reaction mixture is stirred at ambient temperature for 24 hours and then 140 ml of 1N hydrochloric acid is added and stirring continued for an additional 24 hours. The reaction mixture is basified, filtered, the organic layer separated, and the aqueous layer washed with ether and acidified to effect a brown solid which is filtered, washed with water, dried and then recrystallized from acetonitrile to give a tan solid, mp 177°-178° C., of 4,10-dihydro-10-oxofurano[3,2-c][1]benzoxepin-8-acetic acid.

Analysis: Calculated for $C_{14}H_{10}O_5$: 65.11%C; 3.90%H. Found: 65.29%C; 3.96%H.

EXAMPLE 5 a. A mixture of 3.6 g of ethyl 2-bromomethylnicotinate (50% product), 2.7 g of ethyl 4-hydroxyphenylacetate, 8.3 g of potassium carbonate and 0.2 g of sodium iodide in 60 ml of butanone is treated according to the manipulative procedure described above in Example 1(a) to produce a beige solid which is recrystallized from methanol and then washed with a 1:10 mixture of acetonitrile and ether to give white crystals, mp 185°-187° C., of 4-(3-carboxy-2-pyridylmethoxy)phenylacetic acid.

b. By following the manipulative procedure described above in Example 1(b) a sample of 4-(3-carboxy-2-pyridylmethoxy) phenylacetic acid is treated to produce 5,11-dihydro-11-oxopyrido[2,3-c][1]benzoxepin-9-acetic acid.

EXAMPLE 6 a. To a suspension of 10.9 g of ethyl 4-formyl-1,2,5-trimethylpyrrole-3-carboxylate in 40 ml of methanol is added dropwise under nitrogen 5.6 g of sodium borohydride in methanol while maintaining the reaction temperature below 50° C. after total addition the reaction mixture is stirred at ambient temperature for 4 hours, then 90 ml of water introduced and the reaction mixture saturated with potassium carbonate and extracted with ether. The combined ether extracts are dried and concentrated in vacuo leaving a yellow solid which is recrystallized from cyclohexane to give ethyl 4-(hydroxymethyl)-1,2,5-trimethylpyrrole-3-carboxylate, mp 184°-186° C.

b. 1.0 g of ethyl 4-(hydroxymethyl)-1,2,5-trimethylpyrrole-3-carboxylate is dissolved in 15 ml of benzene and 0.6 g of thionyl chloride is added dropwise and after total addition the reaction mixture is stirred for 3.5 hours at ambient temperature. The benzene is removed in vacuo leaving the gray solid, ethyl 4-(chloromethyl)-1,2,5-trimethylpyrrole-3-carboxylate.

c. A mixture of 1.1 g of ethyl 4-(chloromethyl)-1,2,5-trimethylpyrrole-3-carboxylate, 0.9 g of methyl 4-hydroxyphenyl acetate and 0.29 gm of sodium methoxide in 30 ml of methanol is stirred at ice bath temperature for 5 hours and then at ambient temperature for an additional 19 hours. The mixture is filtered, and the filtrate concentrated in vacuo leaving an oil. The oil is dissolved in ether and the ether solution washed with 5% sodium hydroxide and water, dried, and the ether removed leaving a yellow oil. To a solution of the oil in 40 ml of ethanol is added 5 ml of water and 8 g of potassium hydroxide and the reaction mixture refluxed for 16 hours and then concentrated in vacuo. The aqueous solution is cooled, and acidified with ice cold concentrated hydrochloric acid to provide 4-(4-carboxy-1,2,5-trimethyl-3-pyrrylmethoxy)phenylacetic acid.

d. By following the manipulative procedure outlined above in Example 1(b) a sample of 4-(3-carboxy-1,2,5-trimethylpyrrylmethoxy)phenylacetic acid is converted to 4,10-dihydro-1,2,3-trimethyl-10-oxopyrrolo[3,4-c][1]benzoxepin-8-acetic acid.

We claim:

1. A compound of the formula

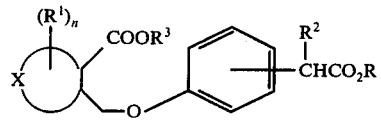

wherein X together with the carbon atoms to which it is attached is a furano ring structure; R is hydrogen or straight or branched chain alkyl of from 1 to 5 carbon atoms; $R^1$ is alkyl of 1 to 4 carbon atoms; $R^2$ is hydrogen or methyl; $R^3$ is hydrogen or alkyl of 1 to 4 carbon atoms; n is the integer 0, 1 or 2; and salts thereof prepared from pharmaceutically acceptable bases.

2. A compound of the formula

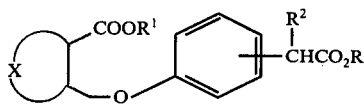

wherein X together with the carbon atoms to which it is attached is a furano ring structure; R is hydrogen or straight or branched chain alkyl of from 1 to 5 carbon atoms; $R^1$ is hydrogen or alkyl of 1 to 4 carbon atoms; and $R^2$ is hydrogen or methyl; and salts thereof prepared from pharmaceutically acceptable bases.

3. A compound defined in claim 2 of the formula

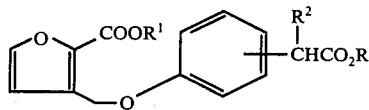

in which R, $R^1$ and $R^2$ are as defined in claim 2; and salts thereof prepared from pharmaceutically acceptable bases.

4. The compound defined in claim 3 which is 4-(2-carboxy-3-furylmethoxy)phenylacetic acid.

* * * * *

UNITED STATES PATENT AND TRADEMARK OFFICE
CERTIFICATE OF CORRECTION

PATENT NO. : 4,101,559
DATED : July 18, 1978
INVENTOR(S) : McFadden et al.

It is certified that error appears in the above–identified patent and that said Letters Patent are hereby corrected as shown below:

Column 1, line 6, "4,025,926" should be --4,025,640--;

Column 5, line 67, "...theinyl..." should be --...thienyl...--;

Column 6, line 65, "...carboxy-b3-furyl..." should be --...carboxy-3-furyl...--.

Signed and Sealed this

Fifteenth Day of May 1979

[SEAL]

Attest:

RUTH C. MASON
Attesting Officer

DONALD W. BANNER
Commissioner of Patents and Trademarks